(12) United States Patent
Capelle et al.

(10) Patent No.: US 10,494,335 B2
(45) Date of Patent: Dec. 3, 2019

(54) METHOD FOR MAKING METHIONINE

(71) Applicant: ADISSEO FRANCE S.A.S., Antony (FR)

(72) Inventors: Nicolas Capelle, Corbas (FR); Patrick Rey, Lyons (FR)

(73) Assignee: ADISSEO FRANCE S.A.S., Antony (FR)

( * ) Notice: Subject to any disclaimer, the term of this patent is extended or adjusted under 35 U.S.C. 154(b) by 2 days.

(21) Appl. No.: 15/567,742

(22) PCT Filed: Apr. 15, 2016

(86) PCT No.: PCT/FR2016/050883
§ 371 (c)(1),
(2) Date: Oct. 19, 2017

(87) PCT Pub. No.: WO2016/170252
PCT Pub. Date: Oct. 27, 2016

(65) Prior Publication Data
US 2018/0111899 A1    Apr. 26, 2018

(30) Foreign Application Priority Data
Apr. 21, 2015  (FR) ..................... 15 53547

(51) Int. Cl.
*C07C 319/20*   (2006.01)
*C07C 319/28*   (2006.01)
(Continued)

(52) U.S. Cl.
CPC ............ *C07C 319/20* (2013.01); *C07B 41/02* (2013.01); *C07C 319/28* (2013.01); *C07C 323/58* (2013.01)

(58) Field of Classification Search
CPC ..... C07B 41/02; C07C 319/20; C07C 319/28; C07C 323/58
See application file for complete search history.

(56) References Cited

U.S. PATENT DOCUMENTS 2,557,920 A  * 6/1951  White ................. C07D 209/20
548/499
4,391,987 A    7/1983  Spindler et al.
(Continued)

FOREIGN PATENT DOCUMENTS

GB    1296347    * 11/1972

OTHER PUBLICATIONS

International Search Report dated Jul. 14, 2016 re: Application No. PCT/FR2016/050883; pp. 1-2; U.S. Pat. No. 2,557,920 A, U.S. Pat. No. 6,126,972 A.

*Primary Examiner* — Amy C Bonaparte
(74) *Attorney, Agent, or Firm* — Cantor Colburn LLP

(57) ABSTRACT

The invention concerns a continuous process for manufacturing methionine by alkaline hydrolysis of methionine hydantoin in aqueous phase, removing $NH_3$ and $CO_2$ of the hydrolysis medium, and neutralizing the obtained methioninate salt, according to which, after removal of $NH_3$ and $CO_2$, the hydrolysis reaction medium is concentrated to precipitate $Na_2CO_3$, said $Na_2CO_3$ being separated then recycled for alkaline hydrolysis, the latter being carried out in the presence of NaOH and $Na_2CO_3$.

11 Claims, 1 Drawing Sheet

Block diagram of the method of the invention comprising a step for separating and recycling sodium carbonate

(51) Int. Cl.
*C07B 41/02* (2006.01)
*C07C 323/58* (2006.01)

(56) References Cited

U.S. PATENT DOCUMENTS

| | | | | | |
|---|---|---|---|---|---|
| 6,126,972 A | * | 10/2000 | Korfer | ............... | C07C 319/20 426/2 |
| 2010/0121104 A1 | * | 5/2010 | Azemi | ............... | C07C 319/20 562/559 |

* cited by examiner

Block diagram of the method of the invention comprising a step for separating and recycling sodium carbonate
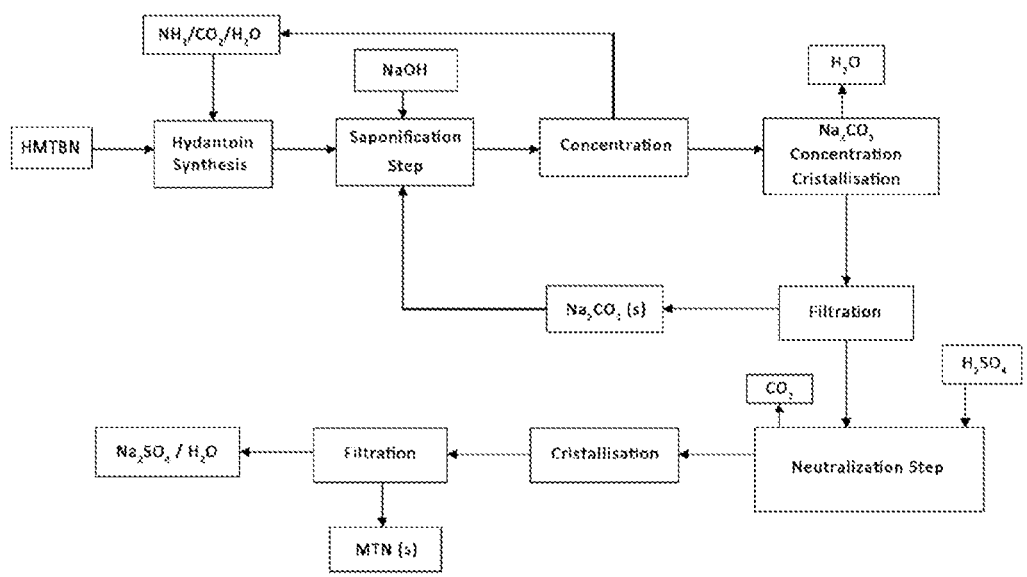

METHOD FOR MAKING METHIONINE

TECHNICAL FIELD

The invention relates to an improvement of the process for manufacturing methionine from the methionine hydantoin.

BACKGROUND

Methionine is a human essential amino acid, so it must be provided by its diet. But its major market is the one of animal nutrition for which it is produced in hundreds of thousands of tons per year. It is essentially manufactured by chemical synthesis.

One of the known chemical processes for obtaining methionine, see for example U.S. Pat. No. 2,557,920A, includes a step of converting methionine hydantoin by alkaline hydrolysis, or saponification, into methioninate salt, then neutralizing the latter into methionine. The hydrolysis of the methionine hydantoin is carried out in the presence of soda and/or of sodium carbonate, in aqueous phase. It occurs as a simultaneous removal of carbon dioxide and ammonia which leads to the methionine salt, sodium methioninate. Carbon dioxide and ammonia are removed from the hydrolysis medium, then the hydrolysis reaction medium containing the methioninate salt is neutralized by sulfuric acid to lead to methionine. The latter is then separated and purified by crystallization.

The conventional reaction conditions of the aforementioned steps are as follows:

The alkaline hydrolysis may be carried out in the presence of an excess of sodium hydroxide, from 1.3 to 3.5 eq., preferably from 1.7 to 2.5 eq., for temperatures comprised between 150 and 200° C.

After removal of ammonia and carbon dioxide from the saponification medium, the neutralization is generally carried out by adding concentrated sulfuric acid until a pH comprised between 3 and 6 is obtained at temperatures comprised between 70 and 130° C. Methionine can then be purified by crystallization, thereafter, by cooling. Methionine is then separated from formed sodium sulfate, by filtration at 30-50° C.

The predominant drawback of this synthesis is the formation of large volumes of sodium sulfate, at the end of the neutralization, which cannot be recycled in the process for manufacturing methionine and which are difficult to recover.

The prior art provides some answers to this problem, with processes for manufacturing aqueous solutions of sodium methioninate which are used instead of solid methionine. According to these processes, a saponification of the methionine hydantoin in the presence of soda is carried out, and a portion of sodium carbonate formed during the alkaline hydrolysis is separated and can be recycled in the saponification step, enabling to obtain a methioninate aqueous solution less concentrated in sodium carbonate. Thus, according to U.S. Pat. No. 4,391,987A, sodium carbonate is separated by cold precipitation, at a temperature ranging from −10° C. to 5° C. This has the disadvantage of using refrigerants and having to cool a saponification solution being at more than 100° C., resulting in a significantly high energy cost. U.S. Pat. No. 6,126,972A provides an improvement of this separation by concentrating the saponification solutions in order to hot-precipitate (100-130° C.) sodium carbonate and separate it by hot-filtration (100-130° C.). The purpose of this separation is to obtain sodium methioninate which can be granulated thereafter via a fluidized bed.

DESCRIPTIONS OF EMBODIMENTS OF THE INVENTION

The invention relates to the development of a process enabling the production of highly pure solid methionine which has the advantage of being much more effective for animal nutrition, at equal weight, than its salt, the sodium methioninate, and so far, is still not remedied to the excessive co-production of sodium sulfate during the neutralization of methioninate into methionine.

The invention provides a solution with a process for manufacturing methionine including an additional step enabling to significantly reduce the amount of formed sodium sulfate. This process can be implemented on the industrial scale via a continuous or discontinuous process. The methionine yields are nearly quantitative and the quality of methionine is not affected by the provided modification.

Thus, the method of the invention comprises alkaline hydrolysis of methionine hydantoin in aqueous phase, the removal of $NH_3$ and $CO_2$ from the hydrolysis medium, and the neutralization of the methioninate salt, said method including a step of concentrating the hydrolysis reaction medium, after removing $NH_3$ and $CO_2$, this concentration allowing precipitating $Na_2CO_3$, said $Na_2CO_3$ being separated then recycled in the previous alkaline hydrolysis step. The alkaline hydrolysis step of the method of the invention is thus carried out in the presence of NaOH and $Na_2CO_3$, which allows, on the one hand, significantly reducing the required amount of soda, this reduction being compensated by a supply of sodium carbonate from the method itself, and on the other hand, decreasing the amount of sodium sulfate formed at the end of the neutralization. A lowering by 20 to 50% (m/m) of the amount of sodium sulfate per kg of produced methionine may be measured.

The hydrolysis medium comprises sodium methioninate and sodium carbonate which have different solubility profiles, depending on the temperature and on their respective concentrations. The difficulty lies in a reproducible compromise between a crystallization of a maximum amount of sodium carbonate and that of a minimum amount of sodium methioninate which will allow determining the conditions of neutralization of methioninate into methionine. The inventors have first observed that a step of extracting sodium carbonate could be inserted in an industrial method for the synthesis of methionine in order to solve the sodium sulfate coproduction problem and they have further defined the optimal conditions under which the compromise above was reached in order not to affect the yield of the neutralization step for obtaining methionine. They are described below and can be considered alone or in combination.

Advantageously, the concentration or enrichment, of the medium in sodium carbonate is carried out by removing water from the medium up to a concentration of the methioninate salt ranging from 20 to 70%, advantageously from 30 to 50% expressed by mass of sodium methioninate with respect to the mass of the medium. Any technique well known to those skilled in the art can be implemented to concentrate the medium. A water removal by evaporation at a temperature ranging from 90 to 100° C., under atmospheric pressure, is particularly effective. It allows a crystallization of a maximum amount of sodium carbonate while maintaining a maximum methioninate salt content in solution in the medium for the subsequent neutralization step. According to another variant, water removal is performed by vacuum evaporation at a temperature ranging from 30 to 90° C., preferably from 40 to 60° C.

The medium of alkaline hydrolysis of the hydantoin may comprise pure methionine hydantoin, unpurified or partially purified hydantoin, from its synthesis medium. Methionine hydantoin can be obtained from 2-hydroxy-4-methylthiobutyronitrile (HMTBN). In this case, it is preferably not isolated from the reaction medium and the latter is directly subjected to the saponification conditions. It is then preferable that the proportion of methionine hydantoin in said reaction medium is at least 10%. Advantageously, a prior removal of ammonia and carbon dioxide, produced during the methionine hydantoin synthesis, is carried out.

Preferably, for alkaline hydrolysis of methionine hydantoin, the molar ratio of the sum of the bases on the sum of sulfur products (Na/S) is at least 2, preferably comprised between 2.5 and 4. Such a ratio allows achieving saponification yields higher than 98%. It allows in particular limiting the formation of the methionine dipeptide. The amount of sulfur is, of course, mostly provided by the methionine hydantoin from the reaction medium where it is formed from HMTBN; it also comes, in minor amounts, from unconsumed HMTBN and from methionine hydantoin present as impurities in the recycled sodium carbonate and introduced in the saponification medium. The sodium is provided by the added soda as a saponification reagent and by sodium carbonate recovered at the end of the concentration of the hydrolysis medium, and recycled. Preferably, the molar ratio $NaOH/Na_2CO_3$ in the hydrolysis medium ranges from 0.5 to 3, preferably from 1 to 2.

Crystallized sodium carbonate in the hydrolysis medium is separated by any technique well known to those skilled in the art, for example by filtration. According to an advantageous variant of the method of the invention, sodium carbonate is filtered at a temperature ranging from 70 to 130° C., preferably from 90 to 110° C. This hot filtration is performed after a sufficient concentration of the saponification flow in order to precipitate the desired amount of sodium carbonate.

In a preferred implementation of the method of the invention, after separation, the recovered $Na_2CO_3$ is previously dissolved in the removed water during the concentration of the hydrolysis medium in sodium carbonate, then recycled in the step of hydrolyzing methionine hydantoin.

The sodium methioninate flow can thereafter be neutralized by sulfuric acid as in the conventional methionine manufacturing process, but also by carbon dioxide, in the form of pressurized gas, which allows neutralizing the medium in the form of sodium bicarbonate and methionine, which precipitates from the medium and may be separated by filtration. The neutralization is advantageously performed at a temperature ranging from 10 to 60° C.

The method of the invention is illustrated in the following examples, in support of the following single FIGURE.

The FIGURE shows the methionine synthesis block diagram integrating a step of concentrating the hydrolysis medium in sodium carbonate, according to the invention. Methionine is manufactured from 2-hydroxy-4-methylthiobutyronitrile (HMTBN) which is converted into methionine hydantoin by any known technique, such as an ammoniacal hydrolysis, in the presence of ammonium bicarbonate. Methionine hydantoin is thereafter saponified by soda, then the saponification liquor is neutralized. According to the invention, a step of concentrating the saponification liquor is thus added, it allows precipitating the sodium carbonate, which is separated from the sodium methioninate by filtration, is brought back into aqueous suspension then recycled in the saponification step. Compared to the conventional method, the sodium sulfate co-production is greatly reduced.

Example 1: Saponification Step

In an autoclave, 92 g of soda at 50% (m/m), 52 g of sodium carbonate and 520 g of methionine hydantoin synthesis flow, containing 139 g of hydantoin and derivatives (hydantoic acid, methioninamide, ureido-butyramide) are loaded. The medium is heated at 180° C. for 30 min, the autogenous pressure amounts to 10 bar. After cooling, the assay of the reaction medium by liquid phase chromatography allows calculating a methionine yield of more than 98%. Before being engaged in the concentration step for the purposes of crystallizing sodium carbonate, the saponification flow is pre-concentrated by stripping with nitrogen.

Example 2: Step of Separating Sodium Carbonate 1100 g of a saponification flow derived from the above prior concentration and containing 150 g of sodium methioninate and 110 g of sodium carbonate is concentrated at 90-110° C. by evaporation. 600 g of water containing ammonium carbonate are thus removed. The resulting medium, in which a portion of sodium carbonate was precipitated, is filtered at 90° C. under nitrogen pressure (150 mbar). 165 g of a solid containing sodium carbonate and sodium methioninate is separated, which can be recycled to the saponification step. 340 g of mother liquor containing 125 g of sodium methioninate are recovered for the next neutralization step.

Example 3: Step of Neutralizing/Crystallizing Methionine

In a reactor, 740 g of sodium carbonate filtration mother liquors obtained in example 2, containing 190 g of sodium methioninate and 50 g of sodium carbonate which did not crystallize in the previous step are loaded. The obtained medium is neutralized at 90-100° C. up to a pH~4.5 by adding 135 g of sulfuric acid at 92.5%. Methionine is crystallized in the flow by cooling at 40° C. It is separated by filtration under nitrogen pressure and after washing with 100 g of water, 200 g of liquor containing 2.2% of methionine are obtained. After drying at 100° C., 170 g of methionine dry cake are obtained at 95% purity and containing 4% of residual sodium sulfate.

The invention claimed is:
1. A continuous process for manufacturing methionine comprising
    carrying out alkaline hydrolysis of methionine hydantoin in an aqueous phase, in the presence of NaOH and $Na_2CO_3$,
    removing $NH_3$ and $CO_2$ from the hydrolysis medium,
    concentrating the hydrolysis medium to precipitate $Na_2CO_3$, said $Na_2CO_3$ being separated then recycled for alkaline hydrolysis, and
    neutralizing the hydrolysis medium with sulfuric acid,
    wherein the process reduces the amount of sodium sulfate produced by 20 to 50% (m/m) compared to a process lacking the concentrating step.
2. The process according to claim 1, wherein the hydrolysis medium prior to the neutralizing step contains a methioninate salt and the concentrating step is carried out by removing water from the hydrolysis medium until the concentration of the sodium methioninate salt from 20 to 70% by mass with respect to the mass of the hydrolysis medium.

3. The process according to claim 2, wherein the water removal is performed by evaporation at a temperature ranging from 90 to 110° C., under atmospheric pressure.

4. The process according to claim 2, wherein the water removal is performed by vacuum evaporation at a temperature ranging from 30 to 90° C.

5. The process according to claim 1, wherein $Na_2CO_3$ is separated by filtration at a temperature ranging from 70 to 130° C.

6. The process according to claim 2, wherein after separation of precipitated $Na_2CO_3$, the precipitated $Na_2CO_3$ is dissolved in the removed water and then recycled to the hydrolysis of methionine hydantoin.

7. The process according to claim 1, wherein the molar ratio of Na/S for the alkaline hydrolysis of methionine hydantoin is at least 2.0.

8. The process according to claim 7, wherein the molar ratio of $NaOH/Na_2CO_3$ ranges from 1 to 3.

9. The process according to claim 1, wherein the hydrolysis medium is neutralized at a temperature ranging from 10 to 60° C.

10. The process according to claim 1, wherein methionine hydantoin is obtained in a reaction medium from 2-hydroxy-4-methylthio-butyronitrile (HMTBN) and the methionine hydantoin is not isolated from the reaction medium prior to alkaline hydrolysis.

11. The process according to claim 10, wherein the proportion of methionine hydantoin in said reaction medium is at least 10% by mass with respect to mass of said reaction medium.

* * * * *